United States Patent [19]

Schwarz et al.

[11] 3,978,230

[45] Aug. 31, 1976

[54] ARTHROPOD MATURATION INHIBITORS

[75] Inventors: Meyer Schwarz, Kensington; Philip E. Sonnet, Bowie; Nobel Wakabayashi, New Carrollton, all of Md.

[73] Assignee: The United States of America as represented by the Secretary of Agriculture, Washington, D.C.

[22] Filed: Mar. 24, 1975

[21] Appl. No.: 561,585

Related U.S. Application Data

[62] Division of Ser. No. 436,239, Jan. 24, 1974, Pat. No. 3,904,773, which is a division of Ser. No. 104,781, Jan. 7, 1971, Pat. No. 3,824,319.

[52] U.S. Cl. ............................ 424/331; 424/DIG. 12
[51] Int. Cl.$^2$ ........................................... A01N 9/24
[58] Field of Search ..................... 424/331, DIG. 12

[56] References Cited
UNITED STATES PATENTS

| | | | |
|---|---|---|---|
| 3,671,558 | 6/1972 | Siddall et al. | 260/410.9 |
| 3,681,385 | 8/1972 | Siddall | 260/327 |
| 3,706,733 | 12/1972 | Henrick et al. | 260/327 E |
| 3,824,319 | 7/1974 | Schwarz et al. | 424/278 |
| 3,904,773 | 9/1975 | Schwarz et al. | 424/304 |

OTHER PUBLICATIONS

Borkduer, Insect Chemosterivats, vol. VII, (1966), pp. 61–63.

*Primary Examiner*—Leonard Schenkman
*Attorney, Agent, or Firm*—M. Howard Silverstein; William E. Scott; David G. McConnell

[57] ABSTRACT

A number of terpenoid compounds and their epoxides were synthesized and found to prevent insect maturation when applied to insects in an immature stage of growth.

2 Claims, No Drawings

ARTHROPOD MATURATION INHIBITORS

This is a division of application Ser. No. 436,239, filed Jan. 24, 1974, now U.S. Pat. No. 3,904,773 which is a division of Ser. No. 104,781, filed Jan. 7, 1971, now U.S. Pat. No. 3,824,319, issued July 16, 1974.

This invention relates to the control of arthropods, especially insects, and more particularly to compounds and to the preparation of compounds which exhibit juvenile hormone activity by stimulation of larval development and inhibition of methamorphosis.

In view of the concern throughout the world regarding the persistence of many insecticides and insecticide residues in our environment and the potential hazard that these materials represent to human populations and furthermore, in view of the fact that many species of insect pests have become resistant or immune to insecticides, the need for more selective agents to meet the problems is evident.

Many of the substances that exhibit juvenile hormone activity possess a terpenoid skeleton. These compounds such as farnesol methyl ether and the juvenile hormone isolated from Hyalphora cecropia (L), methyl 10,11-oxido-3,11-dimethyl-7-ethyl trideca-2,6-dienoate, prevent the formation of sexually mature adults when applied at extremely low dosage levels either topically to the insect in the pupal stage or as a fumigant.

An object of this invention is to provide selective agents for control of insect pests.

Another object is to provide new chemical compounds that prevent insect maturation when applied to insects in an immature stage of growth.

In general, according to the present invention compounds of the general formula

in which Y is

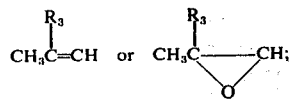

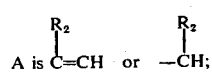

n is a number from 1 to 2;

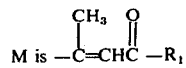

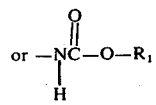

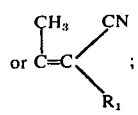

$R_1$ is a straight chain alkyl group of from 1 to 2 carbon atoms, a cycloalkyl group, a phenyl group, a substituted phenyl group, $COOCH_3$, or $CN$; and $R_2$ and $R_3$ are straight chain alkyl groups of from 1 to 2 carbon atoms, are synthesized and found to prevent insect maturation when applied to insects in an immature stage of growth.

In the following discussion regarding preparation of the compounds, the compound numbers referred to are the same as those in the table showing juvenile hormone activity.

Compound 1 is prepared by reacting a carboxylic acid of the formula

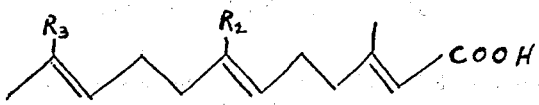

with a excess of an organo-lithium compound in which the organic group can be alkyl, alkinyl, alkynl or aryl. Compound 3 is then prepared by epoxidation of compound 1 with a peracid. Alternatively 1 may be prepared from

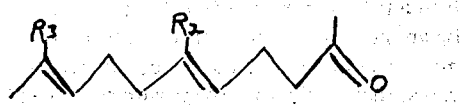

using the Wadsworth-Emmons reaction (J. Amer. Chem. Soc. 83, 1733 (1971)) to produce

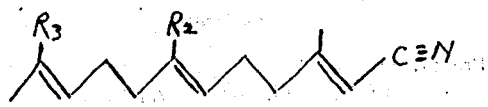

The latter product may then be treated with either an organo-Mg-halogen (Grignard reagent) or an organolithium compound to yield the desired compound 1 (the organic group is same as above). Compounds 5 and 7 are prepared from the appropriate amines,

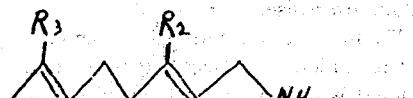

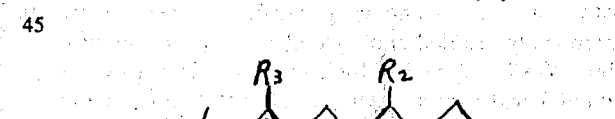

respectively and the appropriate chloroformate $ClCOOR_1$, ($R_1$ as above), in the presence of a tertiary base such as triethylamine, which serves as a hydrogen chloride acceptor. The required amines are prepared by reduction of the oximes of the aldehydes.

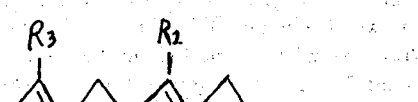

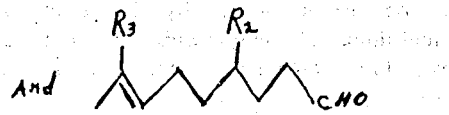

using lithium aluminum hydride [Helv. Chim. Acta. 37, 881 (1954)].

Again the epoxides 6 and 8 are readily prepared from the olefinic precursors 5 and 7 using peracid in an inert solvent. Compound 10 is prepared by the condensation of

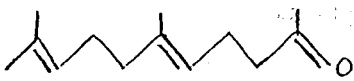

with a malonic acid derivative in the presence of ammonium acetate (J. Amer. Chem. Soc. 63, 3452 (1941). Again, 11 is obtained by epoxidation of 10 using a peracid.

The present invention provides a method for the control of insects, which comprises contacting the insects with one of the compounds in a sufficient amount to effect the normal development of said insects through their metamorphic stages. The materials may be applied to the site of insect infestations by the same methods that are used to broadcast conventional pesticides, that is, diluting them with inert solid carriers or dissolving them in inert organic solvent or oil, or emulsifying them in water.

The following examples illustrate the present invention.

EXAMPLE 1

Preparation of 3,7-tridecadien-2-one, 11,12-epoxy, 4,8,12-tri-methyl. (Compound 3).

To an ice cold suspension of sodium hydride (2,4 g) in 200 ml N,N-dimethylformamide was added dropwise with stirring while the reaction mixture is kept between 0° and 10°C, 17.0 g diethyl cyanomethylphosphonate. When the hydrogen evolution ceased, the temperature was kept below 15°C and 19.0g geranyl acetone was added dropwise.

The mixture was allowed to stand overnight and then it was added to a large excess of cold water and extracted with hexane. The hexane extract was washed with water, dried and evaporated. The residue was fractionally distilled and yielded 15 g of farnesonitrile (bp 94°–97°/0.2 mm) which was converted to Compound 1 as follows: to an ice cold solution of methyl magnesium iodide, prepared from magnesium (0.6 g) and methyl iodide (4.5 g) in 100 ml anhydrous ethyl ether, was added dropwise 5.4 g farnesonitrile. After the addition was complete the reaction mixture was reluxed for 2 hours, allowed to stand overnight, and then decomposed by dropwise addition of excess aqueous ammonium chloride. The ether layer was evaporated and the residue was distilled to yield 3.0 g of Compound 1 bp 105°–110°/0.4 mm. Compound 1 (200 mg) was treated at 0°C with m-chloroperbenzoic acid (200 mg) in 10 ml methylene dichloride to yield compound 3 after extraction of the m-chlorobenzoic acid with dilute aqueous sodium carbonate and removal of the methylene dichloride. The resultant product is highly active against many insect species. Compound 3 can be further purified by distillation, gas-liquid or liquid-liquid chromatography. These processes however, do not enhance the activity to a measurable extent.

EXAMPLE 2

Preparation of 3,7-Tetradecadien-2-one, 11,12-epoxy-8-ethyl-4,12-dimethyl. (Compound 4).

Methyl-3,11-dimethyl-7-ethyltrideca-2,6,10-trienoate (Braun et al. J. Econ. Entomol. 61, 866 (1968) (2 g) was saponified with 1.5 g KOH in 50 ml 80% ethanol. The acid was isolated from the reaction mixture by acidification and extraction with ether. An ether solution of the acid (1 g) was treated with an excess of methyl lithium in hexane (5 ml of a 1.6 molar solution). The ketone, Compound 2 (0.5 g), was obtained after the reaction mixture was decomposed with an aqueous solution of ammonium chloride, followed by evaporation of the ether and molecular distillation (100° (bath)/0.5 mm). Epoxidation and workup, as described in example 1, yielded Compound 4 which had extremely high juvenile hormone activity.

EXAMPLE 3

Preparation of carbamic acid, 3,7-dimethyl-6,7-epoxy-ethyl ester. (Compound 8).

3,7-Dimethyloct-6-enal (15.4 g) in 50 ml ethyl alchohol was added to a solution of hydroxylamine hydrochloride (7 g) and sodium carbonate (5 g) in 25 ml of water. The mixture was heated on the steambath for 15 minutes and then allowed to cool. Addition of an excess of water yielded 3,7-dimethyloct-6-enal oxime as an oil. The oil was extracted with ether and the organic layer dried and evaporated. The residue was added dropwise to a solution of lithium aluminum hydride (3.8 g) in 380 ml anhydrous ethyl ether. After refluxing overnight an additional quantity of lithium aluminum hydride (0.78 g) was added to complete the reduction. Decomposition of the reaction mixture with excess aqueous sodium hydroxide (200 ml of 10% solution), separation of the ether layer, and distillation yielded 3,7-dimethyloct-6-enyl amine (10 g) bp 60°/0.5 mm). To an ice cold solution of this amine (1.5 g) and triethylamine (1.1 g) in ether (25 ml) was added dropwise a solution of ethyl chloroformate (1.1 g) in ether (10 ml). The reaction mixture was allowed to stand overnight at room temperature. The triethylamine hydrochloride was filtered off and the ether solution washed with water, dilute hydrochloric acid, and again with water. The ether solution was dried and evaporated and the residue distilled to yield 2 g carbamic acid (3,7-dimethyl-6-octenyl)-, ethyl ester (Compound 7), bp 102-103/0.1 mm. The ester was epoxidized as described in the previous examples to yield VII. The crude reaction product can be readily purified by chromatography using neutral activated alumina.

EXAMPLE 4

Synthesis of 2 6-dodecadienoic acid, 2-cyano-10,11-dimethyl-, methyl ester (Compound 11).

Geranyl acetone (10 g), methyl cyano acetate (6 g), ammonium acetate (2 g) and acetic acid (1 ml) were refluxed in 200 ml benzene using a Dean-Stark water separator. After 2 hours of refluxing, one additional gram of ammonium acetate was added and the refluxing continued for 2 additional hours. The solution was cooled, washed with water and dried and then the solvent was removed. The residue was distilled to yield 2,6,10-dodecatrienoic acid 2-cyano-3,7,11-trimethyl-, methyl ester (11 g), bp 125°–130°/.1 mm (Compound 10). Epoxidation of the above product as described previously yielded the compound 11.

EXAMPLE 5

Malononitrile (1,5.9-trimethyl-8,9-epoxydec-4-enylidene) (Compound 12).

A solution of geranyl acetone (10 g), malononitrile (4 g), ammonium acetate (.5 g) and acetic acid (0.5 g) is refluxed, using a Dean-Stark trap for 1 hour. The reaction mixture was allowed to cool, then it was washed with water and dried and the benzene removed. The residue was distilled to yield malononitrile-(1,5,9-trimethyl, decadi-4,8-enylidene) (9 g), bp 120°–125°/.3 mm. Epoxydation of the above as described previously yielded compound 12.

TABLE 1

Juvenile Hormone Activity of Representative Compounds on Tenebrio molitor pupae

| Compound | Minimum weight (in μg) of compound needed when applied topically to pupae to make the resultant mature insect incapable of reproduction |
|---|---|
| 1. | 0.3 |
| 2. | 0.01 |
| 3. | 0.03 |
| 4. | 0.001 |
| 5. | 3.0 |
| 6. | 0.1 |
| 7. | 3.0 |
| 8. | 0.1 |

TABLE 1-continued

Juvenile Hormone Activity of Representative Compounds on Tenebrio molitor pupae

| Compound | Minimum weight (in μg) of compound needed when applied topically to pupae to make the resultant mature insect incapable of reproduction |
|---|---|
| 9. | 0.03 |
| 10. | 1.0 |
| 11. | 0.1 |
| 12. | 1.0 |

We claim:

1. A method of preventing the maturation of Tenebrio molitor pupae comprising applying to the pupae a maturation inhibiting amount of a compound of the formula

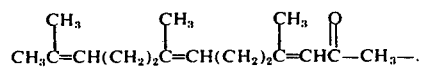

2. A method of preventing the maturation of Tenebrio molitor pupae comprising applying to the pupae a maturation inhibiting amount of a compound of the formula

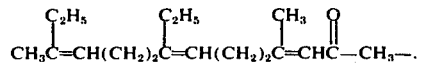

* * * * *